United States Patent [19]
Lee

[11] Patent Number: 5,646,091
[45] Date of Patent: Jul. 8, 1997

[54] REHMANNIA GLUTINOSA EXTRACT AND A SAFENER COMPOSITION HAVING SAFENER ACTIVITY TO A HERBICIDE PARAQUAT

[76] Inventor: Hee Sul Lee, Eunma Apt. 16-603, 318, Daechi-dong, Kangnam-ku, Seoul, Rep. of Korea

[21] Appl. No.: 491,698

[22] Filed: Jun. 19, 1995

[30] Foreign Application Priority Data

Jun. 20, 1994 [KR] Rep. of Korea .......... 94-13950

[51] Int. Cl.⁶ ............................ A01N 25/32
[52] U.S. Cl. ............................ 504/108
[58] Field of Search ...................... 504/108

[56] References Cited

U.S. PATENT DOCUMENTS 4,618,495 10/1986 Okuda et al. .......... 424/195.1
4,919,846 4/1990 Nakama et al. .......... 252/542

OTHER PUBLICATIONS

"Resistance of the medicinal plant jiwhang (*Rehmannia glutinosa*) on Paraquat" J.S. Kim and J.C. Chun, Dec. 1992, The Korean Journal of Weed Science, vol. 12, No. 4. pp. 374–379.

"Comparison in Tolerance to Quinclorac among Followed–by Crops of Paddy Rice," Y.I. Kuk, S.U. Noh and J.O. Guh, Dec. 1992, The Korean Journal of Weed Science, vol. 12, No. 4. p. 380.

*Primary Examiner*—S. Mark Clardy
*Attorney, Agent, or Firm*—Keck, Mahin & Cate

[57] ABSTRACT

The present invention relates to an extract from *Rehmannia glutinosa* plant having a safener activity to a herbicide paraquat, a safener composition and a method for using the same. When the extract or the safener composition of the present invention is treated before treatment of the herbicide or with the herbicide simultaneously, phytotoxicity to the target crops can be reduced or prevented and the crops can be protected.

10 Claims, 3 Drawing Sheets
(5 of 5 Drawing(s) in Color)

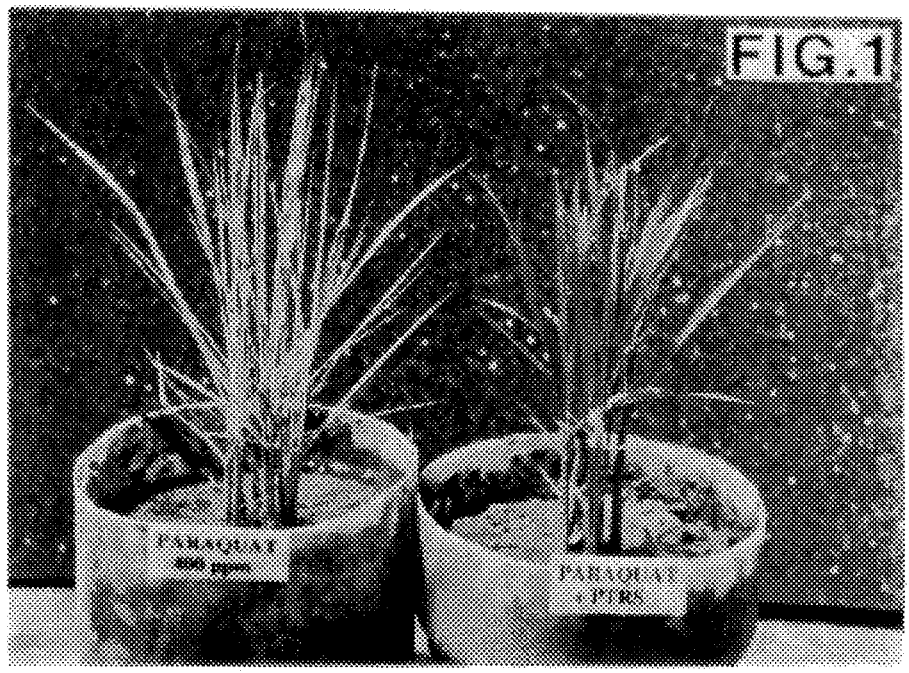
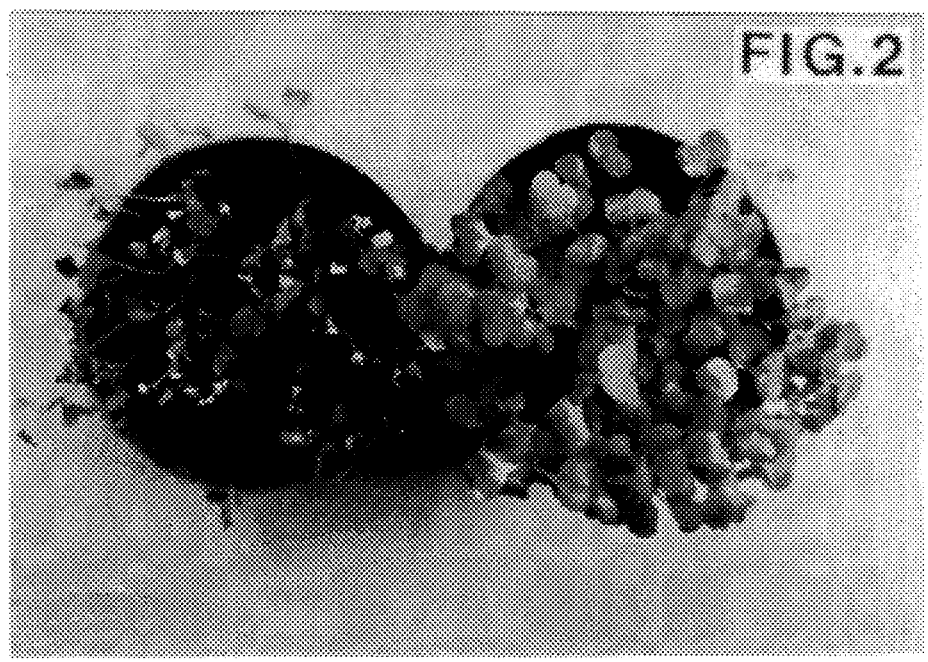

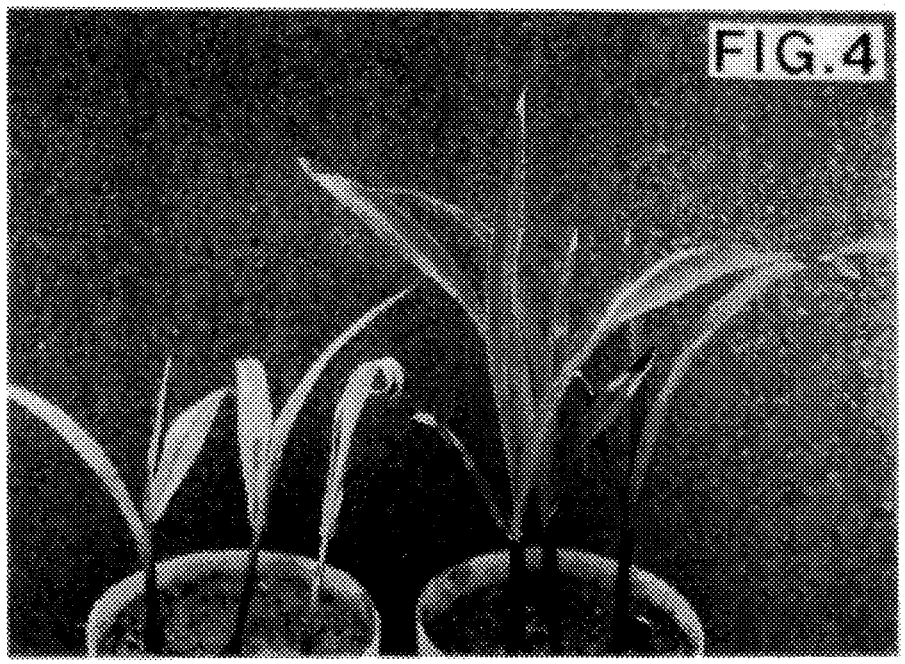

REHMANNIA GLUTINOSA EXTRACT AND A SAFENER COMPOSITION HAVING SAFENER ACTIVITY TO A HERBICIDE PARAQUAT

BACKGROUND OF THE INVENTION

The present invention relates to an extract obtained from *Rehmannia glutinosa* plant having a safener activity to a herbicide paraquat, a safener composition and a method of using the same.

The paraquat uses as a herbicide withers almost all of the green plants non-selectively. When the paraquat is spread on weeds, target farm crops also are damaged by phytotoxicity because of its non-selective characteristics.

In farm cultivation, enormous time and effort are required to control the weeds. In large scale cultivation, usually herbicides are used for weed control. Herbicides can be classified in a selective herbicide which attacks weeds selectively without causing serious damage on crops and a non-selective herbicide which attacks all of the plants in the area where the herbicide is spread. However, excellent selective herbicides are rarely exist and most of the herbicides are non-selective type. Herbicides also could be classified in a soil residual type herbicide and a foliage spray type herbicide according to the spray method. Soil residual type herbicides are used before the germination of the weeds, and thus are less harmful to, plant. However, these are relatively expensive and weeds control efficacy decreases in line with the growth of weeds. Foliage spray type herbicides are relatively cheap, however selective foliage spray herbicide has never been reported yet.

As an outstanding non-selective herbicide, the paraquat is the foliage spray type herbicide which may wither most of the green plants in such a short time of about two days. The paraquat withers the plants by directly inhibiting from the metabolism of cells through formation of superoxide anion in their body. The paraquat is used globally due to its strong weeds control efficacy, however, its use spectrum is considerably restricted due to its non-selective characteristic.

"Safener" is a general term of products designed and prepared for easy use of herbicides through reducing or preventing phytotoxicity of the crops which providing sufficient weed control effects.

Of course, this concept can be applied to insecticides or fungicides. In fact, however, most of the cases are for herbicides. The paraquat—the outstanding foliar spray type non-selective herbicide is used world widely due to its strong weeds control efficacy, however, its use spectrum is considerably restricted due to its non-selective characteristic.

Accordingly, if a safener showing excellent effect to the paraquat is provided, time and effort for weed control could be considerably lightened.

To provide sufficient plant protection performance, it is required that the safener has excellent penetration and translocation capability when it is foliar sprayed. In addition, spreading, wetting, sticking and rain-fastening characteristics is also to be excellent so that the safener may not be lost or degraded at the surface of the leaves for a sufficient time.

The paraquat withers most of the green plants, but certain weeds were found to have resistance to the paraquat.

A medicinal plant, *Rehmannia glutinosa* is reported to have a resistance on the paraquat in Korean Journal of Weed Science vol. 12, No. 4, pp 374–379, with the title of "Resistance of the medicinal plant Jiwhang (*Rehmannia glutinosa*) on paraquat."

After perceiving the specific resistance of *Rehmannia glutinosa* on the paraquat and studying on using *Rehmannia glutinosa* extract as a safener on the paraquat, the present inventor has obtained *Rehmannia glutinosa* extract having good safener activity to the paraquat and found that components such as stachyose have the safener activity to the paraquat after purifying the extract.

SUMMARY OF THE INVENTION

There is provided in the present invention an extract from *Rehmannia glutinosa* having the safener activity on the paraquat and a safener composition comprising stachyose, stachyose hydrates or a derivative thereof.

There also is provided in the present invention an extract from *Rehmannia glutinosa*, a safener composition comprising stachyose, stachyose hydrate or a derivative thereof which can be stably used as safener against paraquat through reducing or eliminating the phytotoxicity of the paraquat to the intended plants when using the paraquat herbicide, and a method of using the extract or the composition before treatment of the paraquat or with the paraquat simultaneously.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 1 is a photograph showing the result of a biological verification of *Rehmannia glutinosa* extract of the present invention having the safener activity on the paraquat on a chinese cabbage.

FIG. 2 is a photograph showing the result of a biological verification of *Rehmannia glutinosa* extract of the present invention having the safener activity on the paraquat on a chinese cabbage.

FIG. 3 is a photograph showing the result of a biological verification of *Rehmannia glutinosa* extract of the present invention having the safener activity on the paraquat on soybean.

FIG. 4 is a photograph showing the result of a biological verification of *Rehmannia glutinosa* extract of the present invention having the safener activity on the paraquat on corns.

DETAILED DESCRIPTION OF THE INVENTION

Figure 5:
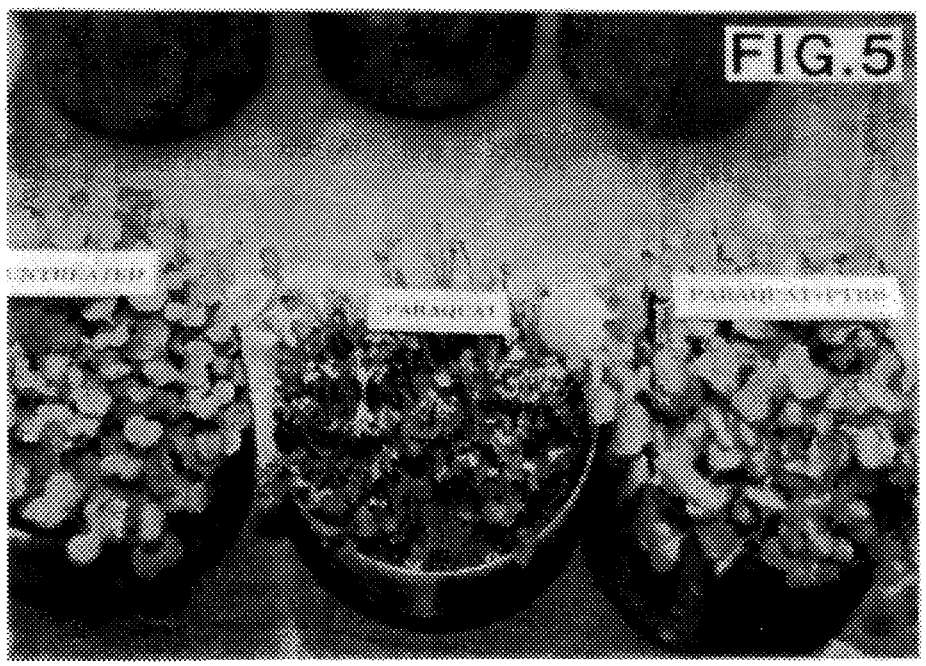
FIG. 5 is a photograph showing the result of a biological verification of stachyose tetrahydrate on a chinese cabbage, which UNTREATED corresponds to the untreated plant, paraquat+PTRS corresponds to the stachyose tetrahydrate and paraquat treated plant and PARAQUAT corresponds to the paraquat treated plant.

The safener composition according to the present invention comprises *Rehmannia glutinosa* extract having the safener activity on *Rehmannia glutinosa*. The *Rehmannia glutinosa* extract of the present invention has the safener activity on *Rehmannia glutinosa* contains stachyose.

The safener composition of the present invention also comprises stachyose, stachyose hydrate, preferably stachyose tetrahydrate or a derivative thereof.

Stachyose is known to be separated from a root of Stachys species, a trunk of a White jasmine, a seed of *Lupinus luteus* and *Soja max*, sap of a western ash tree, etc. (See Dictionary of Natural Products, vol. 5, p 5229, 1994, Chapman & Hall.) Special use of the stachyose has not been reported. However, recently, research on using the stachyose for increasing useful microorganisms in the intestines is carried out.

The stachyose containing extract was extracted from the leaves, the trunks or roots of *Rehmannia glutinosa* in the present invention. However, the origin of the stachyose, stachyose hydrate or a derivative thereof is not limited thereto.

The safener composition of the present invention can further include surfactants or adjuvants to improve the activity.

As for surfactants, non-ionic surfactants those which are non-ionic and/or zwitterionic surfactants those which exhibit both cationic and anionic property could be used. Some anionic surfactants on the contrary inhibit the safener activity of the extract of the present invention. Therefore, cationic surfactants, zwitterionic surfactants or non-ionic surfactants those which do not exhibit any charge is effective. Among these, non-ionic surfactants are preferred.

As for non-ionic surfactants used in the safener composition according to the present invention, $C_{12}$–$C_{18}$ sorbitan aliphatic ester, $C_{12}$–$C_{18}$ polyoxy etylene sorbitan aliphatic ester, $C_{12}$–$C_{18}$ polyoxy ethylene aliphatic ester, polyoxy ethylene resinate, $C_{12}$–$C_{18}$ polyoxy ethylene diester, polyoxy ethylene castor oil, polyoxy ethylene cured castor oil, $C_{12}$–$C_{18}$ polyoxy ethylene alkyl ether, $C_{12}$–$C_{18}$ polyoxy ethylene alkyl phenyl ether, $C_{12}$–$C_{18}$ polyoxy ethylene dialkyl phenyl ether, $C_{12}$–$C_{18}$ polyoxy ethylene alkyl phenyl ether formaline condesate, polyoxy ethylene polyoxy propylene block polymer, $C_{12}$–$C_{18}$ alkyl polyoxy diethylene polyoxy propylene block polymer ether, $C_{12}$–$C_{18}$ alkyl phenyl polyoxy diethylene polyoxy dipropylene block polymer ether, $C_{12}$–$C_{18}$ polyoxy ethylene alkyl amine, $C_{12}$–$C_{18}$ polyoxy ethylene aliphatic amide, polyoxy ethylene bisphenyl ether, polyoxy alkylene (ethylene or propylene) benzophenyl (or phenyl phenyl) ether, polyoxy alkylene (etylene and propylene) styryl phenyl (or phenyl phenyl) ether, polyoxy ethylene ether, ester silicon, fluorine-based surfactant, etc. could be illustrated.

Adjuvants could be used in the present composition to increase the penetration and translocation capability trasporting characteristic. N-alkyl pyrrolidone, alkyl vinyl pyrrolidone copolymer, polyvinyl pyrrolidone homopolymer, etc. could be effectively used. The alkyl here is $C_1$–$C_{12}$.

The present invention also is related to a method for extracting from *Rehmannia glutinosa* or for purifying extract or stachyose tetrahydrate having the safener activity on the paraquat.

The extracting and purifying methods according to the present invention are as follows.

Leaves, trunks or roots of *Rehmannia glutinosa* are cut finely or ground and weighed. 4–5 times by weight of water, a polar solvent or a mixture thereof is added and the mixture is heated to extract.

As for the polar solvent, alcohols such as methanol and ethanol could be used. When using the mixture of water and alcohol as the extracting solvent, the amount of alcohol is 20–80 volume %, preferably 30–60 volume % and more preferably 40–50 volume %.

To increase the purity of extraction, the first extraction with a polar solvent could be repeated using the above mentioned same solvent. The resulting extract from the first extraction is filtered using a common filtering equipment such as cotton stuff, multi layer filter, press filter, etc., and then using a rotational vacuum evaporator or using a common cylindrical vacuum evaporator, membrane vacuum evaporator, etc.

Using a non-polar solvent which is not miscible with water, impurities such as pigments are removed from the concentrated extract. That is, the non-polar solvent is added to the obtained concentrated extract and stirred. After standing for a while, the aqueous layer is collected. As for the non-polar solvents, dichloromethane, methyl acetate, ethyl acetate, chloroform, ethyl ether, iso-octane, cyclohexane, etc. could be used. After repeating the above procedure for two or three times, majority of impurities such as pigments are removed. Two or three times volume of water or a mixture of water and $C_1$–$C_4$ alcohol could be added to facilitate the separation of the aqueous layer from the solvent layer. The obtained extract could be used in field test directly or after diluting in water without further purification. The extract also could be further purified to increase the active ingredient concentration.

Excellent safening effect could be obtained by systematic spray of the paraquat after foliar spray of extract from *Rehmannia glutinosa*. In case of treating the paraquat after spraying the purified extract with or without a surfactant, no phytotoxic symptom in the plant treated with the extract was observed. Untreated plants and weeds were completely withered. In case of treating the extract with a surfactant/adjuvant, the duration time of the plant protection could be lengthened.

Further purification could be carried by the known methods such as HPLC method. After the final purification, stachyose tetrahydrate was confirmed by NMR spectrum thereof comparing with the standard starchyose (Aldrich Chemical Company) and its NMR data in The aldrich library of $^{13}C$ and $^{1}H$ FT-NMR Spectra, 1st ed. vol. 1, p 30. of Aldrich Chemical Company.

The extract could be used as it is or could be concentrated or dried to use in powder form, if needed. The powder could be used as it is or could be diluted to an appropriate concentration for each plant through experiments.

To confirm the safening activity of Rhemannia glutinosa extract and the safener composition containing stachyose or stachyose hydrate on the paraquat according to the present invention, biological verification test was carried out with a plant group including both of the monocotyledon and the dicotyledon.

The extract acts as the safener on the paraquat for all the plants including the monocotyledon and the dicotyledon. Among them, effects for rice, soybean, corn, cotton, chinese cabbage, radish, pineapple, gum tree, coconut, other vegetables and other fruits are especially good.

The present invention also relates to a method for using the safener composition. The safener composition of the present invention could be used in various ways depends of the situation. As for one method, crop seeds are soaked in the diluted solution of the safener composition and, if necessary, dried before sowing.

As for another method, the safener composition of the present invention is diluted in an appropriate concentration and the obtained solution is foliar sprayed on crops. As an example of spraying the safener on the crops, the safener could be sprayed upon the plant to be protected before paraquat treatment.

In extensive agriculture, paraquat is carefully used just at furrows to avoid phytotoxicity on the crops. However, the crops in ridges are damaged by the spattered paraquat. In this case, the crop could be protected while weeds are controlled by pre or simultaneous spray of the extract/ safener composition of the present with the paraquat spray.

Another method is as follows. For transplanting crops like rice, red pepper, chinese cabbage, radish, etc., the extract or the safener composition of the present invention is sprayed before the transplanting or after the transplanting, of the crops on the weed-removed farmland before the weeds grow up. After then paraquat is sprayed when weeds grow.

The present invention will be described in detail by the following examples. However, the present invention is not limited to them.

EXAMPLE 1

Extraction and Purification of the Safener Active Compound 100 g of washed and sliced tuberous roots of *Rehmannia glutinosa* was placed in an 1 l round container having a reflux equipment and then 500 ml of 80% methanol was added. Extraction was proceeded for 6 hours at 80° C. while stirring from time to time. Large lumps were removed using a gauze and the solution was filtered using a filter paper to obtain 500 ml of a filtrate.

The filtrate was concentrated to 100 ml in rotary vacuum evaporator at 200 rpm and 80° C. The obtained extract was viscous dark brown liquid. 300 ml of dichloromethane was added to the obtained concentrated solution and was stirred. After standing for one hour, an aqueous layer was removed. 300 ml of cyclohexane was added to the removed aqueous layer and stirred. After standing for one hour, aqueous layer was removed again. Above procedure was repeated for three times to obtain a first purified extract which has little viscosity and is nearly transparent colorless liquid.

On a 2.0 cm×50 cm column, packed silicagel (200 mesh for chromatography) which has been already equilibrated with ethyl acetate and dichloromethane (60:40, v/v), 30 ml of the first purified extract was loaded.

500 ml of ethyl acetate and propanol mixture (60:40, v/v) was slowly eluted and the same volume of ethyl acetate and propanol mixture (30:70, v/v) was eluted. Among the fractions obtained by eluting 500 ml of methanol and water mixture (95:5, v/v), fractions having the safener activity was collected and concentrated to 30 ml to obtain a second purified extract. The second purified extract showed maximum absorption at UV 280 nm and 330 nm.

EXAMPLE 2

Purification of Stachyose 1 ml of the second purified extract obtained in example 1 was analyzed by HPLC under the following condition. One eminent peak (retention time: 4.87 min) was obtained.

pump: TOSOH, CCPM: detector (at 254 nm): TOSOF, UV8010: column: MERCK, C18, 10×250 mm: flow rate:3.0 ml/min: concentration gradient:0 min ($H_2O$/MeOH=100/0, v/v), 5 min ($H_2O$/MeOH=100/0, v/v), 20 min ($H_2O$/MeOH=0/100, v/v), 25 min ($H_2O$/MeOH=0/100, v/v), 27 min ($H_2O$/MeOH=100/0, v/v), 32 min ($H_2O$/MeOH=100/0, v/v).

NMR data from the fractions of the single peak at the HPLC was as follows.

$^{13}$C-NMR (100MHz): 108.47, 104.48, 98.94, 98.66, 92.84, 81.95, 77.27, 74.85, 73.35, 71.92, 71.58, 70.23, 70.10, 69.99, 69.88, 69.44, 68.93, 68.83, 67.23, 66.55, 63.27, 62.18, 61.72.

$^{13}$H-NMR (400MHz): 5.44 (d, J=3.9Hz,1H), 5.01 (s, 2H), 4.25–3.50 (m, 25H).

EXAMPLE 3

Biological Verification on Rice

Selected rice seeds were soaked, germinated and planted in a rice seedbed to grow to three-leaves stage. 200 plants of rice seedlings in three-leaves stage were transplanted into 20 plastic pots (diameter 9 cm) containing paddy field soil (10 plants were planted in each pot). 20 ml of the second purified extract (350 ml was obtained from 200 g of tuberose root of *Rehmannia glutinosa*) was diluted with 1,000 ml of water. This solution was foliar sprayed on 15 pots. A week later, paraquat was diluted in water to 400 ppm and treated on all the 20 pots. The treatment was carried out by spraying the solution on the plants uniformly using a small sprayer. The five controls were treated only with the paraquat.

The efficacy of the extract from *Rehmannia glutinosa* was judged by whether the necrosis or browning, the typical phytotoxic system of paraquat, was shown or not at extract treated plots, compared to control plots. As known in FIG. 1, for the controls which were treated with the paraquat alone, necrosis was started from after 48 hours and the plants were completely killed after 96 hours. However, for the *Rehmannia glutinosa* extract treated and then the paraquat treated plots, no symptom of phytotoxicity was observed.

EXAMPLE 4

Biological Verification on Chinese Cabbage, Soybean and Corn

Seeds of each plant were sowed in 9 cm plastic pots containing upland soil, respectively. After growing the chinese cabbage and soybean until two leaves stage and corn until three leaves stage, they were treated with the extract diluted at the same rate as example 3. A week later, paraquat diluted to 400 ppm was treated on the whole pots. The treatment was carried out by spraying the solution on the plants uniformly using a small sprayer. The controls were treated with the paraquat only. The efficacy of *Rehmannia glutinosa* extract was visually estimated by observation of occurrence of necrosis or browning, the typical symptom of paraquat phytotoxicity. As shown in FIGS. 2–4, for the controls which were treated with the paraquat alone necrosis was started from after 12–24 hours and the plants were completely killed after 48 hours. However, for the Rhemannia glutinosa extract treated and then the paraquat treated plots, no symptom of phytotoxicity was observed.

EXAMPLE 5

Biological Verification of Stachyose Tetrahydreate

Stachyose tetrahydrate obtained from example 2 was diluted using water to 0.015%. Biological verification of stachyose tetrahydrate on chinese cabbage was carried out with 200 ppm of the paraquat by the method described in example 4 and the result was illustrated in FIG. 5. The above test was done with the standard stachyose tetrahydrate from Wako Pure Chemical Industries, Ltd. in same method, and same result was obtained.

EXAMPLE 6

Preparation of a Safener Composition

A safener composition containing 1.0 volume % of the extract from *Rehmannia glutinosa* of example 1, 25.0 volume % of polyoxy ethylene nonyl phenol ethoxylate, 0.5 volume % of N-dodecil-2-pyrrolidone, 0.5 volume % of polyvinyl pyrrolidone homopolymer and 73.0 volume % of water of prepared.

What is claimed is:

1. A method of treating a plant comprising applying an extract of *Rehmannia glutinosa* having a safener activity to a herbicide paraquat.

2. A method of treating a plant according to claim 1, wherein the extract contains stachyose tetrahydrate.

3. A method of treating a plant comprising applying a safener composition having safener activity to paraquat, wherein the safener composition comprises stachyose, stachyose hydrate or a derivative thereof as a main component.

4. A method of treating a plant according to claim 3, wherein the safener composition comprises stachyose tetrahydrate.

5. A method of treating a plant according to claim 3, wherein the safener composition further comprises at least one surfactant selected from the group consisting of cationic surfactant, zwitterionic surfactant and non-ionic surfactant, or at least one adjuvant selected from the group consisting of N-alkyl ($C_1$–$C_{12}$) pyrrolidone, alkyl ($C_1$–$C_{12}$) vinyl pyrrolidone copolymer and polyvinyl pyrrolidone homopolymer.

6. A method of treating a plant according to claim 5, wherein the amount of said safener composition is about 5–20 weight %, and the amount of said adjuvant is about 1–5 weight %.

7. A method of treating a plant using a safener composition defined in claim 3, comprising treating a plant with said safener composition simultaneously with or prior to treatment with paraquat.

8. A method of treating a plant using a safener composition defined in claim 4, comprising treating a plant with said safener composition simultaneously with or prior to treatment with paraquat.

9. A method of treating a plant using a safener composition defined in claim 5, comprising treating a plant with said safener composition simultaneously with or prior to treatment with paraquat.

10. A method of treating a plant using a safener composition defined in claim 6, comprising treating a plant with said safener composition simultaneously with or prior to treatment with paraquat.

* * * * *